(12) United States Patent
Walsh

(10) Patent No.: US 10,137,017 B2
(45) Date of Patent: Nov. 27, 2018

(54) CRIMPER DEVICE

(71) Applicant: CARDIOVANTAGE MEDICAL, INC., San Mateo, CA (US)

(72) Inventor: Brandon G. Walsh, San Mateo, CA (US)

(73) Assignee: SUZHOU JIECHENG MEDICAL TECHNOLOGY CO., LTD., Wujiang, Jiangsu (CN)

( * ) Notice: Subject to any disclaimer, the term of this patent is extended or adjusted under 35 U.S.C. 154(b) by 0 days.

(21) Appl. No.: 15/404,147

(22) Filed: Jan. 11, 2017

(65) Prior Publication Data

US 2017/0119561 A1     May 4, 2017

Related U.S. Application Data

(63) Continuation of application No. PCT/US2016/045733, filed on Aug. 5, 2016.

(60) Provisional application No. 62/202,710, filed on Aug. 7, 2015.

(51) Int. Cl.
    *B25B 27/14*      (2006.01)
    *A61F 2/95*      (2013.01)

(52) U.S. Cl.
    CPC .......... *A61F 2/95* (2013.01); *A61F 2002/9522* (2013.01)

(58) Field of Classification Search
    CPC .... A61F 2/95; A61F 2002/9522; B23P 11/00; B23P 11/005; B23Q 3/06; B25B 5/00; B25B 13/10; B25B 13/12; B25B 13/18; B25B 13/32; B25B 13/44; B25B 27/146; B25B 7/14
See application file for complete search history.

(56) References Cited

U.S. PATENT DOCUMENTS

| 5,261,263 A * | 11/1993 | Whitesell ............. B25B 27/146 |
| | | 29/237 |
| 6,202,272 B1 | 3/2001 | Jackson |
| 6,309,383 B1 | 10/2001 | Campbell et al. |
| 6,568,235 B1 | 5/2003 | Kokish |
| 2004/0128818 A1 | 7/2004 | Motsenbocker |
| 2007/0068216 A1 | 3/2007 | Kokish |
| 2013/0213185 A1* | 8/2013 | Brown ................... B25B 13/10 |
| | | 81/52 |

FOREIGN PATENT DOCUMENTS

| CN | 1631338 A | 6/2005 |
| CN | 102083392 A | 6/2011 |

OTHER PUBLICATIONS

Chinese Office Action from Chinese Patent Application No. 201680002012.4, dated Dec. 4, 2017, 13 pages.

* cited by examiner

*Primary Examiner* — David Bryant
*Assistant Examiner* — Nirvana Deonauth
(74) *Attorney, Agent, or Firm* — Nathan S. Smith; Andrew N. Khouzam; Morgan, Lewis & Bockius LLP

(57) ABSTRACT

A crimper device can facilitate sheathing of a stent frame for vascular delivery. The device can include first and second components that rotate relative to each other to drive radial movement of one or more compression members of the device. The one or more compression members can direct and balance a compressive force within an aperture of the device. In use, the stent frame can be positioned within the aperture and be compacted by actuation of the compression members.

15 Claims, 12 Drawing Sheets

CRIMPER DEVICE

CROSS-REFERENCE TO RELATED APPLICATIONS

The present application claims the benefit of priority under 35 U.S.C. § 120 as a continuation of International Patent Application Serial No. PCT/US2016/045733 entitled "CRIMPER DEVICE" and filed on Aug. 5, 2016, which claims the benefit of priority under 35 U.S.C. § 119 as a nonprovisional of U.S. Provisional Patent Application No. 62/202,710 entitled "CRIMPER DEVICE", and filed on Aug. 7, 2015, the disclosures of which are hereby incorporated by reference in their entirety for all purposes.

TECHNICAL FIELD

The present inventions relate generally to manufacturing tools, and more specifically, to a handheld tool for crimping a stent by applying a uniform radial force to the circumference of a frame of the stent to reduce the diameter of the stent frame thereby facilitating packing of the stent frame into a tubular sheath.

BACKGROUND

Stents and stent delivery assemblies are utilized in a number of medical procedures and situations, and as such they are well known and widely available in a variety of designs and configurations. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls or, e.g., cardiac valve, while maintaining the vessel in an open, unobstructed condition.

Inflation-expandable stents are well known. Inflation-expandable stents are crimped to their reduced diameter about the delivery catheter, then maneuvered to the deployment site and expanded to the vessel diameter by fluid inflation of a balloon positioned between the stent and the delivery catheter. Alternatively, the stent is a self-expanding stent that acts similarly to a spring and will recover to its expanded or implanted configuration after being released from a compacted condition such as in a sheath. A self-expanding stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. Self-expanding stents can use alloys such as Nitinol (i.e., Ni—Ti alloy) which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Placement of such stents in a body vessel can be achieved by a device which comprises an outer catheter for holding the stent in its compact form.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

The present disclosure is related to the crimping of inflation-expandable or self-expandable stents to facilitate packing of the stent into a sheath for delivery to a diseased vessel or coronary structure such as a diseased valve. Further, the present disclosure is also directed to a device for crimping a stent frame wherein the device comprises a compression assembly. The compression assembly comprises a plurality of compression members which form an aperture, wherein the plurality of compression members are coupled to one another so as to be movable inward or outward simultaneously.

In some embodiments, each of the plurality of compression members comprises a main body and a distal portion, wherein the distal portions of the plurality of compression members forms a central approximately circular aperture.

In some embodiments, when the number of compression members in the compression assembly is n, the angle between each of the adjacent compression member main bodies is about $360/n$. In other embodiments, when the number of compression members in the compression assembly is n, the angle between the main body and engagement arm of each of the plurality of compression members is $[180-(360/n)]$.

In some embodiments, each of the plurality of compression members comprises a tab on the main body of each compression member. In other embodiments, the tab is positioned on the upper surface of the main body of each compression member and the tab is at an angle which is equal to $360/n$. In still other embodiments, when the plurality of compression members moves simultaneously, each tab slides along the outer edge of the distal portion of an adjacent compression member.

In some embodiments, moving the main bodies of the plurality of compression members toward the aperture results in a decrease in the diameter of the aperture while maintaining the approximately circular shape of the aperture.

In some embodiments, the device is a handheld stent crimper comprising the compression assembly, a first arm member and a second arm member. In other embodiments, the first arm member comprises a first handle and a first annular ring and the second arm member comprises a second handle and a second annular ring.

In some embodiments, the second annular ring comprises n slots which are evenly spaced about the inner circumference of the second annular ring.

In some embodiments, moving the first and second handles toward one another results in the simultaneous movement of the plurality of compression members to reduce the diameter of the aperture. In other embodiments, moving the first and second handles away from one another results in the simultaneous movement of the plurality of compression members to enlarge the diameter of the aperture.

In some embodiments, the second arm member comprises a plurality of ports, wherein the number of ports is the same as the number of compression members. The main body of each compression member fits into one of the ports of the second arm member wherein movement of the second arm member toward the first arm member causes the main body of the compression member to move toward the aperture, thereby reducing the diameter of the aperture.

The subject technology is illustrated, for example, according to various aspects described below. Various examples of aspects of the subject technology are described as numbered embodiments (1, 2, 3, etc.) for convenience. These are provided as examples and do not limit the subject technology. It is noted that any of the dependent embodiments may be combined in any combination with each other or one or more other independent embodiments, to form an independent embodiment. The other embodiments can be presented in a similar manner. The following is a non-limiting summary of some embodiments presented herein:

Clause 1. A device for collapsing a stent frame, the device comprising: a stationary first component comprising a first grip section and a first guide section coupled to the first grip section, the first guide section comprising (i) a first central aperture having a first central axis and (ii) a plurality of first elongate guide slots extending in a radial direction from the first central aperture; a movable or rotatable second component comprising a second grip section and a second guide section, the second guide section comprising (i) a second central aperture having a second central axis coaxially aligned with the first central axis and (i) a plurality of driving structures extending about the second central aperture; an alignment mechanism configured to maintain the second central axis coaxially aligned with the central axis of the first central aperture as the second guide section rotates relative to the first guide section; and a plurality of compression members, each comprising a contact surface for engaging an expandable implant, each compression member being slidably positioned at least partially within a respective first elongate guide slot and slidably engaged with a respective driving structure for urging slidable movement of the compression members within the first elongate guide slots as the second guide section rotates relative to the first guide section, thereby moving the contact surfaces between expanded and collapsed positions upon rotation of the second component relative to the first component to increase or decrease a size of a compression aperture formed by the contact surfaces.

Clause 2. The device of Clause 1, wherein the alignment mechanism comprises (i) a plurality of alignment slots in the first or second guide sections and (ii) a plurality of alignment rivets coupled to the first or second guide sections and extending through the alignment slots to maintain the second central axis coaxially aligned with the central axis of the first central aperture as the second guide section rotates relative to the first guide section.

Clause 3. The device of any of the above Clauses, wherein the alignment mechanism comprises a plurality of alignment slots in the second guide section and a plurality of alignment rivets coupled to the first guide section, the plurality of alignment slots extending about the second central aperture, wherein movement of the alignment rivets within the alignment slots maintains the second central axis coaxially aligned with the central axis of the first central aperture as the second guide section rotates relative to the first guide section.

Clause 4. The device of any of the above Clauses, wherein the driving structure comprises a plurality of driving slots in the second guide section.

Clause 5. The device of Clause 4, wherein the driving structure further comprises a plurality of driving rivets, each coupled to a respective compression member and engaged with the plurality of driving slots for urging slidable movement of the compression members within the first elongate guide slots.

Clause 6. The device of any of the above Clauses, wherein the driving structure comprises a plurality of driving protrusions coupled to the second guide section.

Clause 7. The device of Clause 6, wherein the driving structure further comprises a plurality of driving slots, each coupled to a respective compression member and engaged with the driving protrusions for urging slidable movement of the compression members within the first elongate guide slots.

Clause 8. The device of any of the above Clauses, further comprising a stationary third component comprising a third grip section and a third guide section coupled to the third grip section, the third guide section comprising (i) a third central aperture having a third central axis and (ii) a plurality of second elongate guide slots extending in a radial direction from the third central aperture, the third grip section being coupled to the first grip section to thereby align the third central axis with the first and second central axes and the plurality of second elongate guide slots with the plurality of first elongate guide slots.

Clause 9. The device of Clause 8, wherein the alignment mechanism comprises (i) a plurality of alignment rivets coupled to both the first and third guide sections and (ii) a plurality of alignment slots in the second guide section, and wherein the second guide section is interposed between the first and third guide sections to thereby align the third central axis with the first and second central axes.

Clause 10. The device of Clause 9, wherein each of the plurality of second elongate guide slots comprises a longitudinal axis that intersects with the third central axis.

Clause 11. The device of any of the above Clauses, wherein each of the plurality of first elongate guide slots comprises a longitudinal axis that intersects with the first central axis.

Clause 12. The device of any of the above Clauses, wherein each of the plurality of compression members comprises a sliding portion in slidable contact with a portion of the respective first guide slot.

Clause 13. The device of Clause 12, wherein each of the first guide slots comprises a straight edge for contacting the respective sliding portions and facilitating straight radial movement of the compression members relative to the second central axis.

Clause 14. The device of Clause 12, wherein each of the sliding portions comprises a flat surface.

Clause 15. The device of any of the above Clauses, wherein each of plurality of compression members comprises first and second halves, and wherein the rotatable second component is interposed between the first and second halves of each of the compression members.

Clause 16. The device of any of the above Clauses, wherein the first and second halves of the plurality of compression members are identical.

Clause 17. The device of any of the above Clauses, wherein the plurality of compression members comprises an axial engagement mechanism comprising a plurality of engagement slots and engagement arms that extend within the engagement slots to laterally engage adjacent compression members to restrict axial movement of the adjacent compression members with respect to each other.

Clause 18. The device of Clause 17, wherein each compression member comprises an engagement slot and an engagement arm extending laterally from the compression member.

Clause 19. The device of Clause 18, wherein the device comprises six compression members and longitudinal axes of the engagement arms of the compression members extend at angles of about 120 degrees relative to respective longitudinal axes of bodies of the compression members.

Clause 20. A device for collapsing a stent frame, the device comprising: first and second components each having an elongate handle portion and a ring portion, the ring portions each comprising apertures having central axes that are coaxial when the first and second components are coupled together, the first and second components comprising a pin and slot alignment mechanism to permit relative rotation between the first and second components while maintaining the central axes thereof coaxial with each other, wherein the first component comprises guide portions that extend radially outwardly from the central axis of the first component, and wherein the second component comprises driving portions that extend along a circumferential path that converges toward the aperture of the second component; and a plurality of compression members each having a sliding portion and a driven portion, each sliding portion being engaged with a respective guide portion to move radially relative to the central axis of the first component, each driven portion being engaged with a respective driving portion to cause radial movement of the compression member along the guide portion when the first component is rotated relative to the second component.

Clause 21. The device of Clause 20, wherein the guide portions of the first component comprise elongate slots, and wherein the sliding portion of each of the plurality of compression members permits each compression member to move radially within a respective elongate slot of the first component.

Clause 22. The device of any of Clauses 20-21, wherein the driving portions of the second component comprise driving slots, and wherein the driven portion of each of the plurality of compression members comprises a pin coupled to the compression member and slidable within the slot of the second component to permit each compression member to move radially within a respective guide slot of the first component.

Clause 23. The device of any of Clauses 20-22, wherein the first component ring portion comprises opposing halves and an axial space therebetween into which the second component ring portion is positioned to coaxially align the central axes of the ring portions of the first and second components.

Clause 24. A method of collapsing a stent frame, the method comprising: inserting a stent frame, having first and second ends, into a compression aperture of a crimper device; abutting the first end of the stent frame against a radial edge portion of a compression member to longitudinally engage the stent within the compression aperture; collapsing the compression aperture to compress the stent frame; and exerting a longitudinal force against the first end of the stent frame to couple the second end of the stent frame to a delivery assembly.

Clause 25. The method of Clause 24, wherein the collapsing the compression aperture comprises rotating components of the crimper device to induce radial translation of a plurality of compression members to reduce the size of the compression aperture.

Clause 26. The method of any of Clauses 24-25, further comprising locking together a rotating component and a stationary component of the crimper device to maintain the stent frame in the collapsed configuration without simultaneously requiring exertion of a rotational force by the user on the rotating and stationary components.

Additional embodiments of the present devices, will be apparent from the following description, drawings, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present inventions. Additional aspects and advantages of the present inventions are set forth in the following description and claims, particularly when considered in conjunction with the accompanying drawings.

BRIEF DESCRIPTION OF DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

In accordance with some embodiments, the present disclosure provides a handheld device for crimping and sheathing a stent frame. The device can comprise at least two components that rotate relative to each other in order to drive radial movement of a compression mechanism. The device can comprise an alignment mechanism in order to ensure that at least a portion of each of the components is aligned during rotation. Further, the device can also comprise a drive mechanism that converts the rotational motion of the components to a compressive motion that can act against an expanded stent frame.

Figure 1:
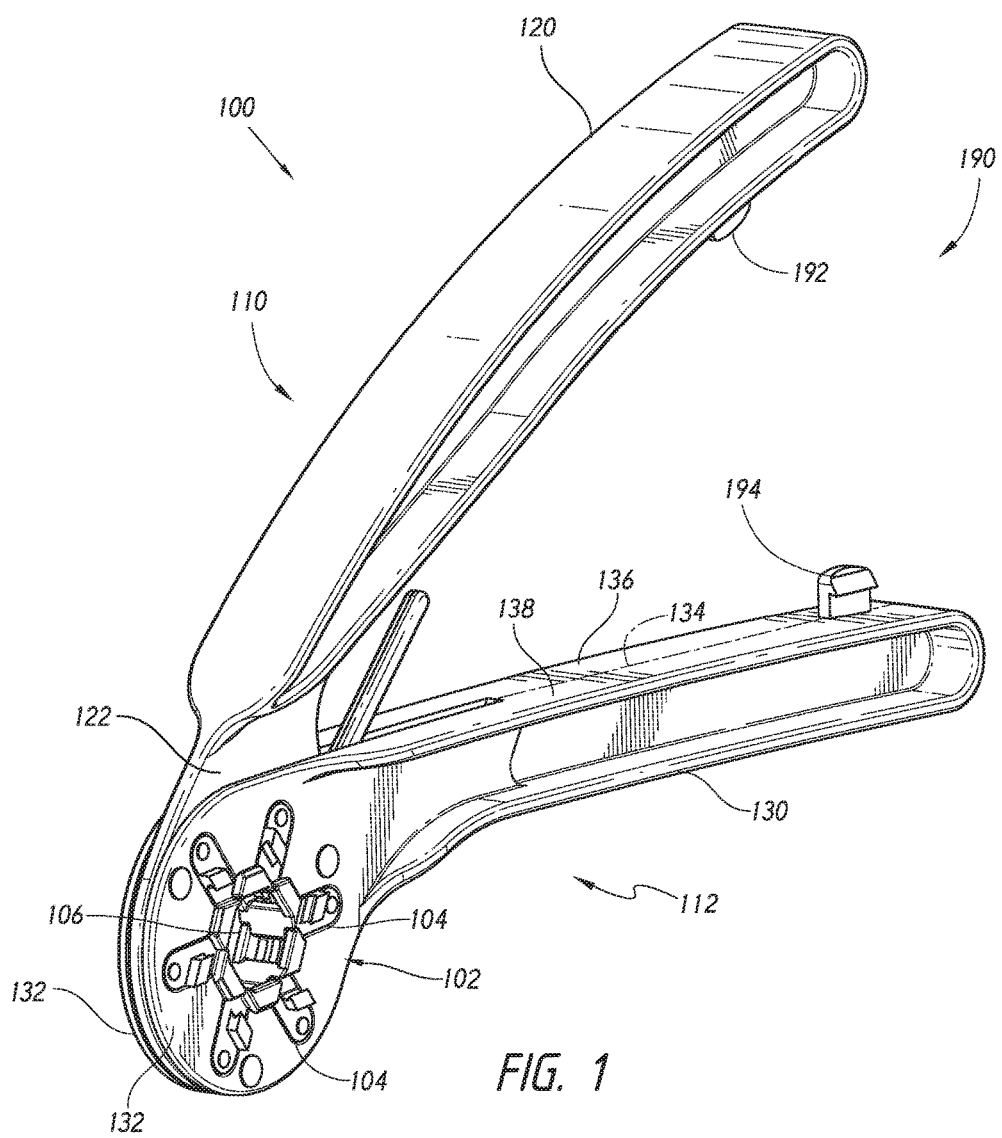
FIG. 1 is a perspective view of a crimper device in an open configuration, according to some embodiments.
Figure 2:
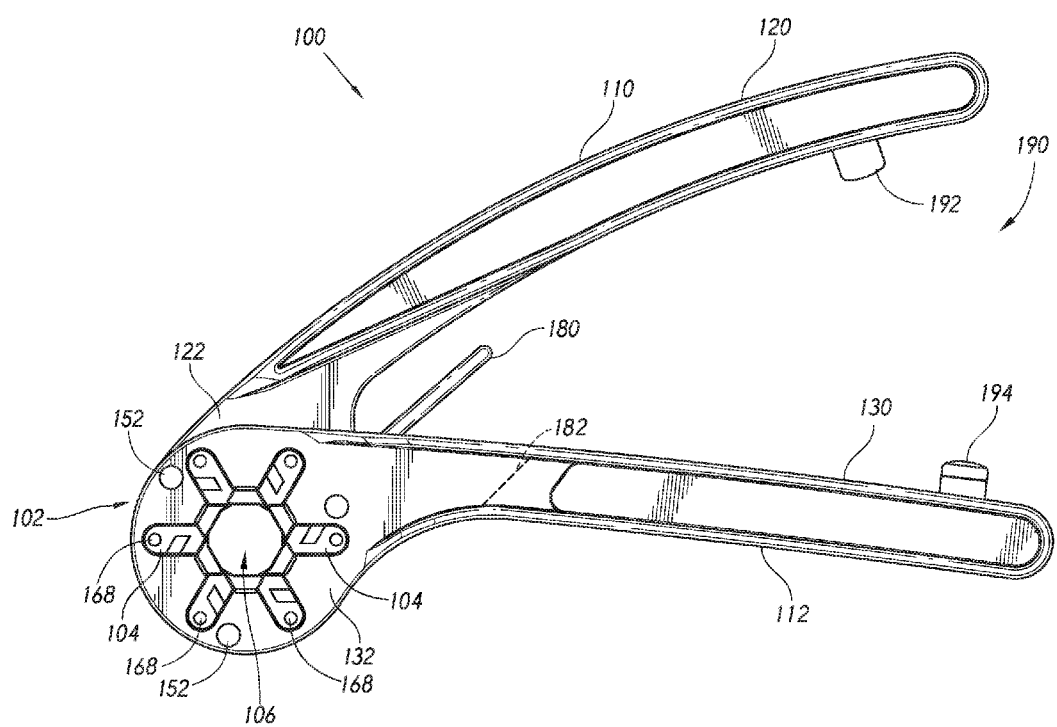
FIG. 2 is a side view of the crimper device of FIG. 1 in the open configuration.

An embodiment of a crimper device 100 is illustrated in FIGS. 1-2. The crimper device 100 can comprise a compression assembly 102 that includes multiple compression members 104 situated to form a central or compression aperture 106. The device 100 can comprise a first, movable or rotatable component 110 and a second, stationary component 112 that are rotatable relative to each other. The compression assembly 102 can be actuated by rotating the rotatable component 110 relative to the stationary component 112. The device 100 can advantageously be formed as a handheld crimper device in which the compression aperture 106 can have a variable-size that can accommodate large and small expanded stent frame diameters and compress the stent frame to a desired final, collapsed configuration.

The rotatable component 110 can comprise a movable grip section 120 and a rotatable guide section 122. Similarly, the stationary component 112 can comprise a stationary grip section 130 and a stationary guide section 132. The grip sections 120, 130 of the rotatable and stationary components 110, 112 can permit a user to hold the device and exert a rotational force that is translated into radial compression. In the present disclosure, the use of the term "stationary" provides a relative frame of reference for the rotatable component and does not limit the stationary component to a table-top-mounted, wall-mounted, or other structure that is mounted or fixed to the floor or to another structure. Instead, as noted, both the rotatable and stationary components 110, 112 can form a hand-held device 100 that is freely movable by a user.

Optionally, one or both of the movable or stationary components 110, 112 can comprise one or more portions. For example, as shown by the dashed line 134 in FIG. 1, the stationary component 112 can comprise first and second halves 136, 138 that can be joined together along the stationary grip section 130 to form a stationary component assembly having a slot or space between stationary guide sections thereof into which the rotating guide section 122 can be inserted and rotatably coupled. Other embodiments can be provided in which the rotatable component 110 comprises two halves and a slot or space is provided between movable guide sections of a rotatable component assembly into which the stationary guide section 132 can be inserted and rotatably coupled. However, some embodiments can comprise combinations of these features and can also provide for rotatable or stationary components formed from a single, continuous piece of material that include a plurality of guide sections and slots or spaces provided for rotatable engagement with a corresponding rotatable or stationary component.

Figure 8:
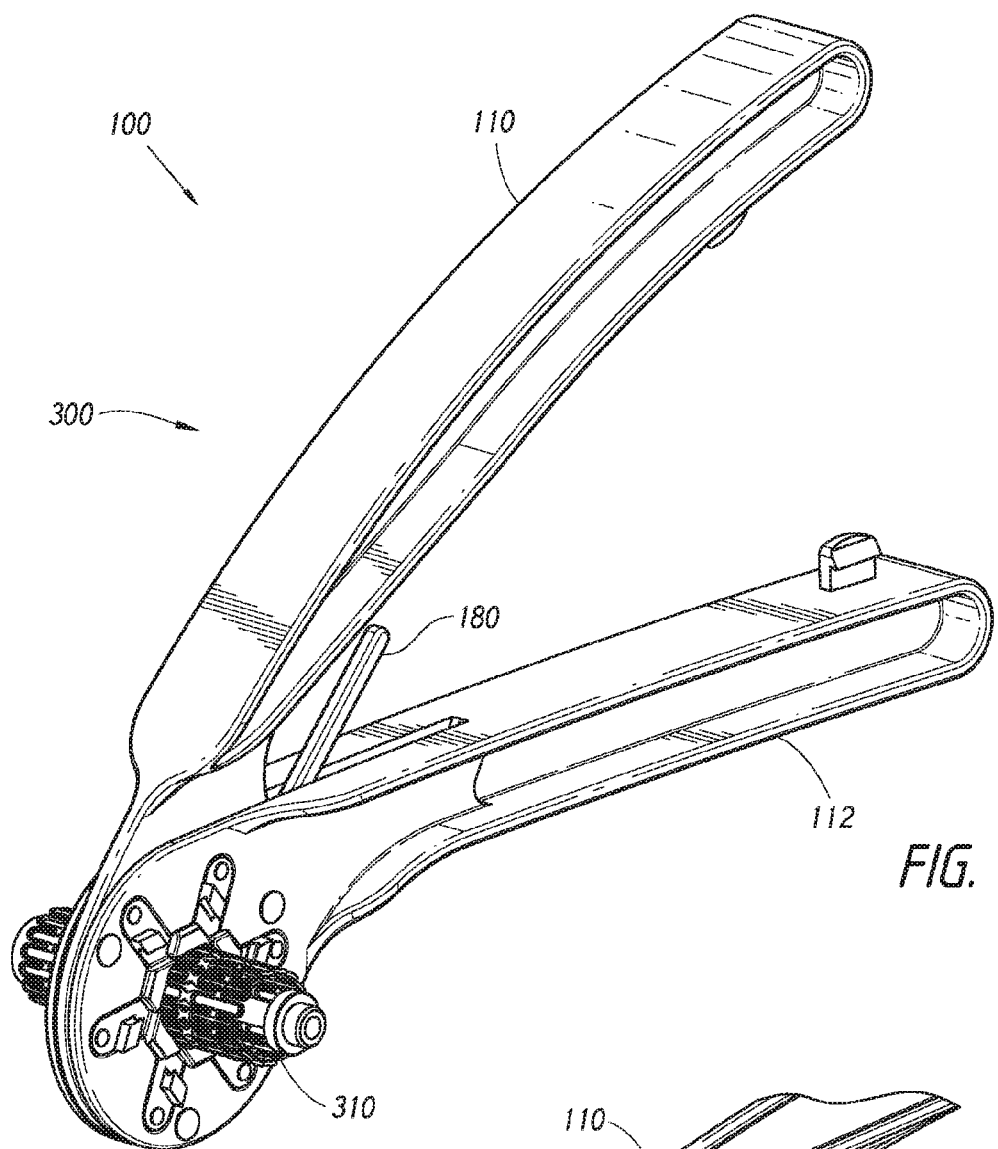
FIGS. 8 and 9 are views that illustrate engagement and initial positioning of a stent frame within a compression aperture of the crimper device of FIG. 1 in the open configuration, according to some embodiments.
Figure 9:
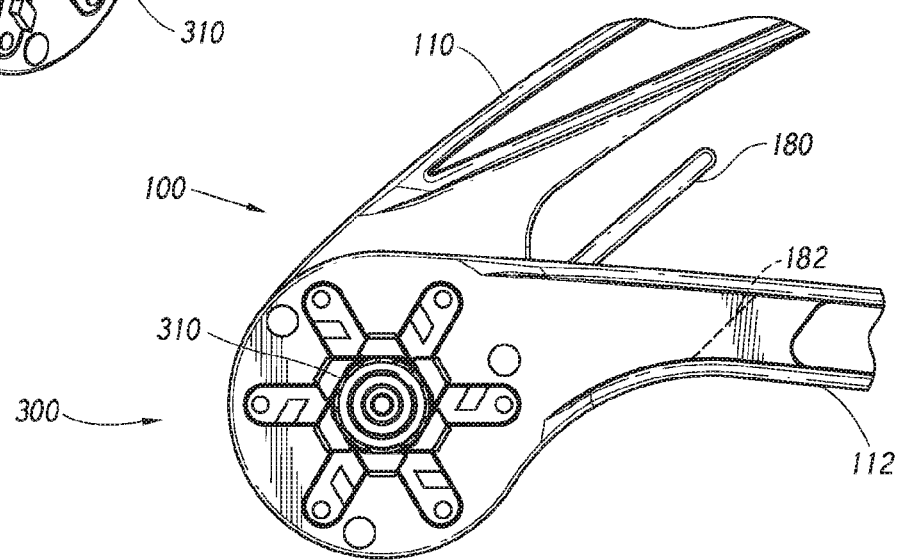
Figure 10:
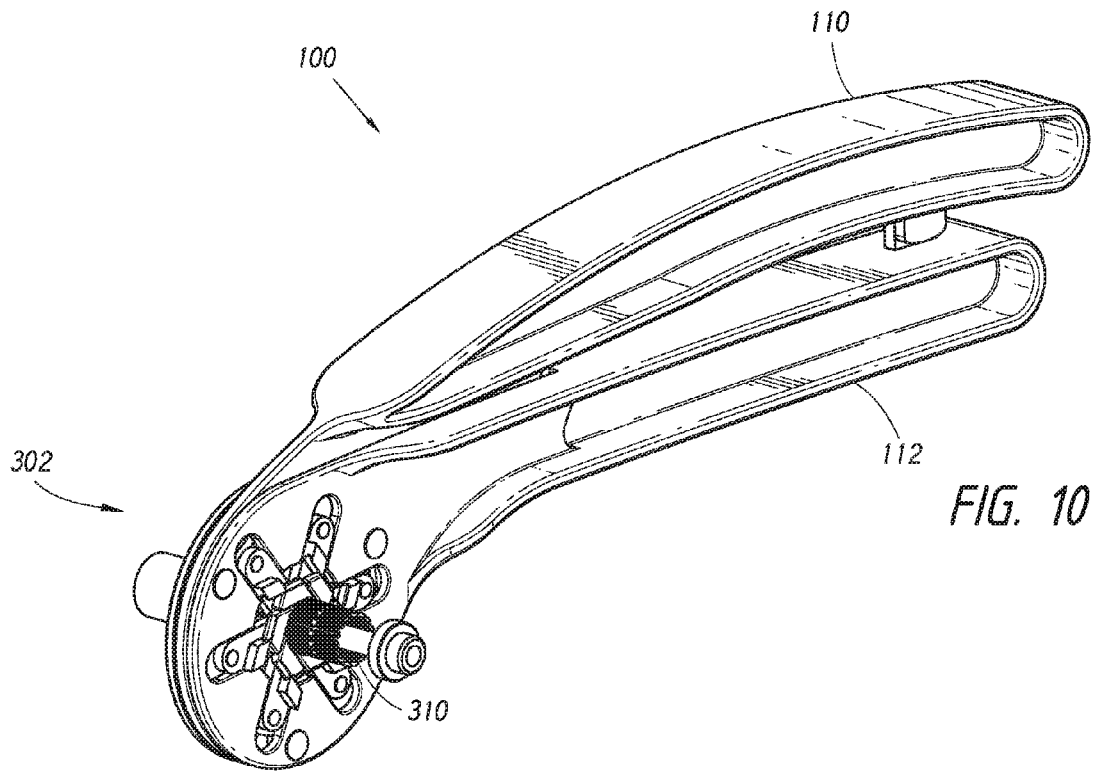
FIGS. 10 and 11 are views that illustrate movement of the crimper device toward a closed configuration in order to collapse the stent frame within the compression aperture, according to some embodiments.
Figure 11:
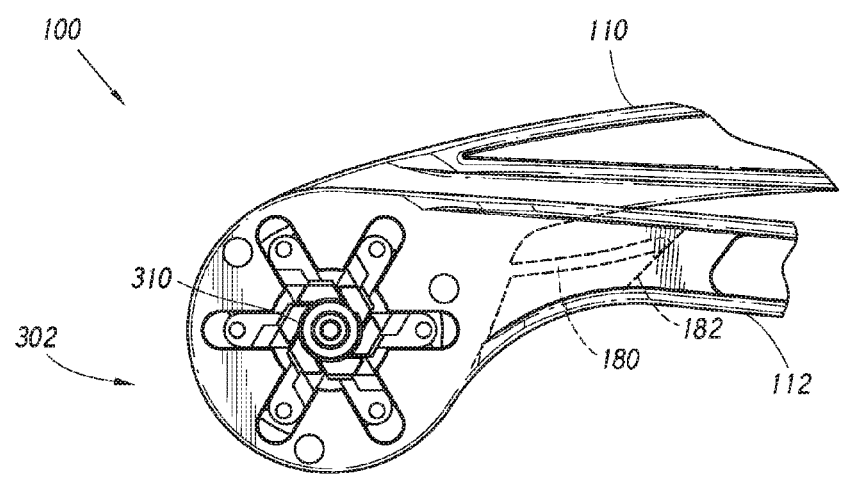

As illustrated in FIGS. 1-4, in some embodiments, the rotatable guide section 122 and the stationary guide section 132 can comprise round or ring-shaped profiles. FIG. 2 illustrates that the profiles of the rotating and stationary guide sections 122, 132 can, in side view, have a common boundary along at least 40% of the perimeter thereof, whether in an open or closed configuration (FIGS. 2, 8, and 9 illustrate the device 100 in an open configuration, and FIGS. 10 and 11 illustrate the device 100 in a closed configuration).

Figure 3:
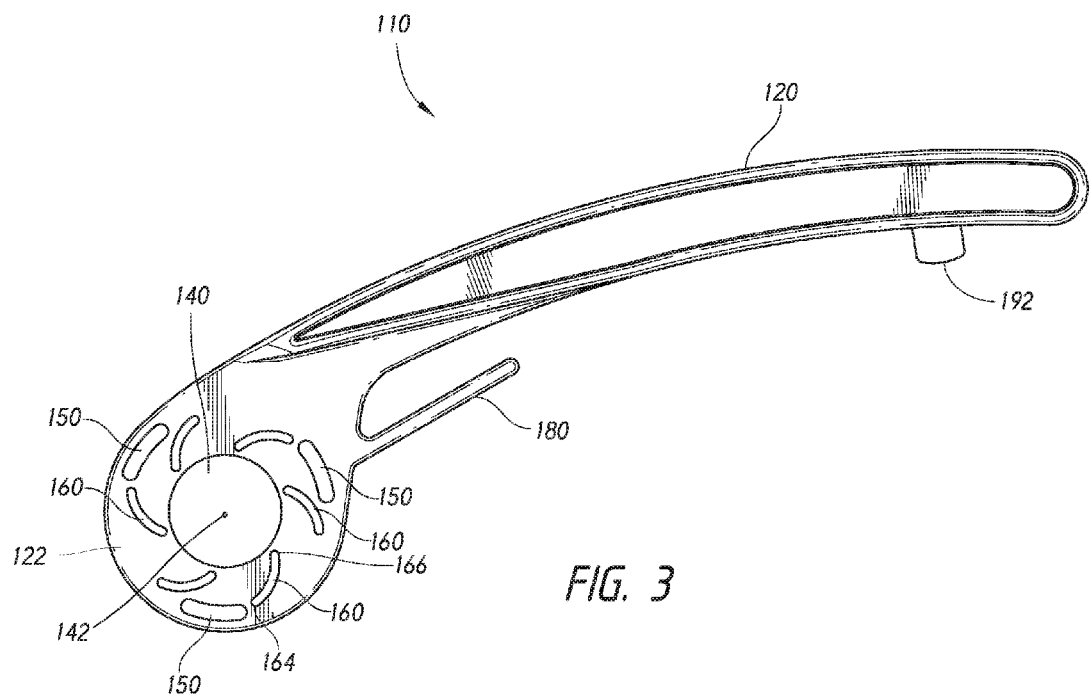
FIG. 3 is a side view of a movable or rotatable component of the crimper device of FIG. 1, according to some embodiments.
Figure 4:
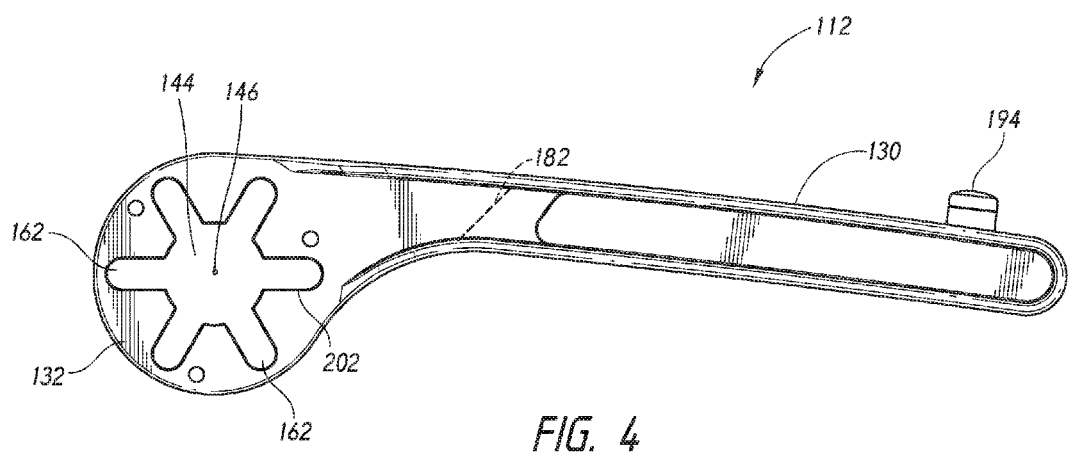
FIG. 4 is a side view of a stationary component of the crimper device of FIG. 1, according to some embodiments.

Referring to FIGS. 3 and 4, the rotatable guide section 122 can comprise a central aperture 140 and a central axis 142 extending through the central aperture 140. The stationary guide section 132 can comprise a central aperture 140 and a central axis 146 extending through the central aperture 140. In its assembled state, the device 100 is configured such that the central axes 142, 146 of the rotatable and stationary guide sections 122, 132 are coaxially aligned relative to each other.

Further, the device 100 can comprise an alignment mechanism that can maintain the coaxial alignment of the central axes 142, 146 during relative rotation of the rotatable and stationary guide sections 122, 132. In some embodiments of an alignment mechanism, the rotatable and/or stationary guide sections 122, 132 can comprise one or more alignment slots or alignment rivets that enable the rotatable and stationary guide sections 122, 132 to be interconnected in a rotatable coupling that aligns and maintains a coaxial alignment of the central axes 142, 146.

For example, as illustrated in FIGS. 2 and 3, the rotatable guide section 122 can comprise a plurality of alignment slots 150 through which alignment rivets 152 can extend. The alignment rivets 152 can be at least partially engaged or coupled to the stationary guide section 132. For example, the alignment rivets 152 can comprise enlarged ends or other adhesive or mechanical means that secure the alignment rivets 152 relative to the stationary guide section 132. The alignment slots 150 can extend about the central axis 142 and each have a substantially constant radius. Further, as illustrated in the embodiment of FIG. 3, the alignment slots 150 can be positioned about the central axis 142 and all share a common, constant radius (although each of the alignment slots 150 can be spaced apart from the central axis 142 at a unique or different radius than another of the alignment slots 150, if desired). Accordingly, when the rotatable guide section 122 rotates relative to the stationary guide section 132, with the alignment rivets 152 sliding within the alignment slots 150, the central axes 142, 146 can maintain a coaxial alignment relative to each other. Further, some embodiments can be configured such that both of the rotatable and stationary guide sections 122, 132 include both alignment slots therein and alignment rivets 152 coupled thereto.

Further, although the alignment mechanism illustrated in FIGS. 2 and 3 utilizes a pin-and-slot arrangement distributed along and interior region of the rotatable and stationary guide sections 122, 132, the alignment mechanism can also comprise one or more structures distributed along the periphery of the rotatable and stationary guide sections 122, 132. For example, the alignment mechanism can comprise one or more clamp components, ridges, or other structures that align a perimeter of one of the rotatable or stationary guide sections 122, 132 relative to the other of the rotatable or stationary guide sections 122, 132. The clamp components, ridges, or other structures can be formed separately from or from a continuous piece of material with either or both of the rotatable or stationary guide sections 122, 132. By aligning the central axes 142, 146 of the rotatable and stationary guide sections 122, 132 by engaging the perimeter of one or both of the rotatable or stationary guide sections 122, 132, and clamping or securing the rotatable and stationary guide sections 122, 132 to restrict movement along the central axes 142, 146, the clamp-type alignment mechanism can provide the same advantages and benefits as the pin-and-slot arrangement disclosed above.

In accordance with some embodiments, the device can comprise a drive mechanism that enables the compression members to move from an expanded profile to a collapsed profile, thus collapsing a profile or diameter of a stent frame. For example, the rotatable and stationary guide sections can rotate to drive radial movement of the compression members. At least one of the rotatable or stationary guide sections can comprise a driving protrusion or slot that extends in a circumferential direction and converges toward the central axis thereof and the other of the rotatable or stationary guide sections can comprise a radial guide, such as a slot or protrusion, along which the compression member can radially translate. The point of intersection of the driving protrusion or slot and the radial guide can move toward or away from the central axis during rotation of the guide sections (depending on the direction of rotation). For example, in some embodiments in which the radial guide comprises a slot, the driving protrusion or slot can be visible through the guide slot and, during rotation of the rotatable and stationary guide sections relative to each other, the visible portion of the driving protrusion or slot can move radially toward or away from the shared central axis of the guide sections.

Referring to FIG. 3, the drive mechanism of the device 100 can urge radial movement of the compression members 104 of the compression assembly 102 in response to relative rotational movement of the rotatable component 110 relative to the stationary component 112. In some embodiments, the rotatable guide section 122 can comprise a protrusion or slot that radially converges toward the central axis 142. FIG. 3 illustrates that the rotatable guide section 122 can comprise a plurality of driving slots 160. As shown, each of the driving slots 160 has a first end 164 and a second end 166, and the first end 164 is positioned radially further from the central axis 142 than the second end 166. As discussed herein, during operation of the device 100, a structure or pin coupled to a compression member (or a pin or rivet 168 that couples the compression member 104 relative to the protrusion or slot, as shown in FIG. 2) can slide within the driving slot 160, moving from the first end 164 toward the second end 166, thus driving the structure or pin closer to the central axis 142.

In order to convert the rotational motion of the rotatable guide section 122 and the movement of the structure or pin within the driving slot 160 into radial movement of the compression member, the stationary guide section 132 can comprise a plurality of guide slots 162 in which the compression members 104 can translate. As shown in the embodiment of FIG. 4, the guide slots 162 can extend in a radial direction away from the central aperture 144, permitting a respective compression member 104 to move radially along a respective guide slot 162, toward or away from the central axis 146.

Accordingly, as the rotatable guide section 122 rotates toward a closed configuration, relative to the stationary guide section 132, the engagement between the driving slot 160 of the rotatable guide section 122 and the structure or pin of a compression member 104 will cause the compression member 104 to move within the guide slot 162. Thus, during rotation of the rotatable guide section 122 relative to the stationary guide section 132 toward the closed configuration, the radial distance between the slot or protrusion of the rotatable guide section 122 and either central axis 142, 144 decreases (or if rotated opposite, increases), as seen through the respective guide slot 162. This decreasing radial distance and engagement between the slot or protrusion and the respective compression member 104 causes the respective compression member 104 to converge toward the central axis 146, resulting in a decreased-diameter compression aperture 106 (compare FIGS. 8 and 9 with FIGS. 10 and 11).

Alternatively, some embodiments can be configured to permit the stationary guide section 132 to comprise a protrusion or slot that radially converges toward the central axis 146, and the rotatable guide section 122 can comprise guide slots that permit the compression members to move therealong in response to relative rotation between the rotatable and stationary guide sections 122, 132. Further, some embodiments can be configured such that both of the rotatable and stationary guide sections 122, 132 includes both guide slots therein and guide rivets coupled thereto.

Various configurations of compression mechanisms can be developed using the teachings herein. For example, although the illustrated embodiments show compression mechanisms in which the compression members do not rotate relative to each other, the compression mechanism can be configured to rotate relative to each other in some embodiments. Indeed, the rotation-to-radial-translation mechanism disclosed herein can be implemented on a unit-by-unit basis for each compression member. Each compression member can therefore slide radially along a respective guide slot in a guide section relative to which the compression member does not rotate, while being radially urged toward or away from a collapsed configuration in response to engagement between the compression member and a guide section relative to which the compression member rotates. Such a system can be implemented on an individual compression member basis, or as a compression mechanism as a whole (as illustrated in the accompanying figures).

In accordance with some embodiments, the device 100 can also comprise a dampener component 180. The dampener component 180 can be configured to provide a degree of resistance to rotation as the device 100 is moving toward the collapsed position. This resistance can advantageously slow rotation of the device 100 and compression of the stent frame when the stent frame is becoming increasingly smaller and an increasingly larger force is required to collapse the stent frame. Thus, the rate of collapsing can be slowed in order to prevent mechanical damage, such as bending or breaking, to the stent frame.

As illustrated in FIGS. 1-4, the dampener component 180 can comprise an elongate, cantilevered protrusion or rod that extends from the rotatable component 110 and contacts a limiter surface 182 of the stationary component 112. Is generally illustrated in FIGS. 8-11, as the rotatable component 110 is moved from the open configuration toward the closed configuration, the dampener component 180 can contact the limiter surface 182. The stiffness of the dampener component 180 can be configured to provide a high degree of initial resistance, a low degree of initial resistance, an increasing amount of resistance upon further rotation, and/or a substantially constant amount of resistance upon further rotation. In some embodiments, the dampener component 180 can advantageously provide a minimal amount of resistance upon initial contact with the limiter surface 182 and, as the dampener component 180 bends, the resistance to rotation can increase, corresponding to the increasingly small size of the compressed stent frame. Accordingly, some embodiments of the device 100 and therefore tend to avoid damage to the delicate configuration of the stent frame.

Optionally, the device 100 can also comprise a locking mechanism 190. The locking mechanism 190 can comprise a first structure 192 coupled to the grip section 120 of the rotatable component 110 and a second structure 194 coupled to the grip section 130 of the stationary component 112. The first and second structures 192, 194 can comprise a combination of protruding hooks (as illustrated in FIGS. 1-4) or a protruding hook and a slot, to permit temporary or permanent engagement between the first and second structures 192, 194. In this manner, the device 100 can be used to compress a stent frame and maintain the stent frame in a collapsed configuration without requiring the user to exert a constant compressive force on the grip sections 120, 130. Once engaged, the locking mechanism 190 can thereby permit the user to attend to other aspects of a method of loading or preparing a stent delivery system onto which the stent frame is being compressed.

Figure 5:
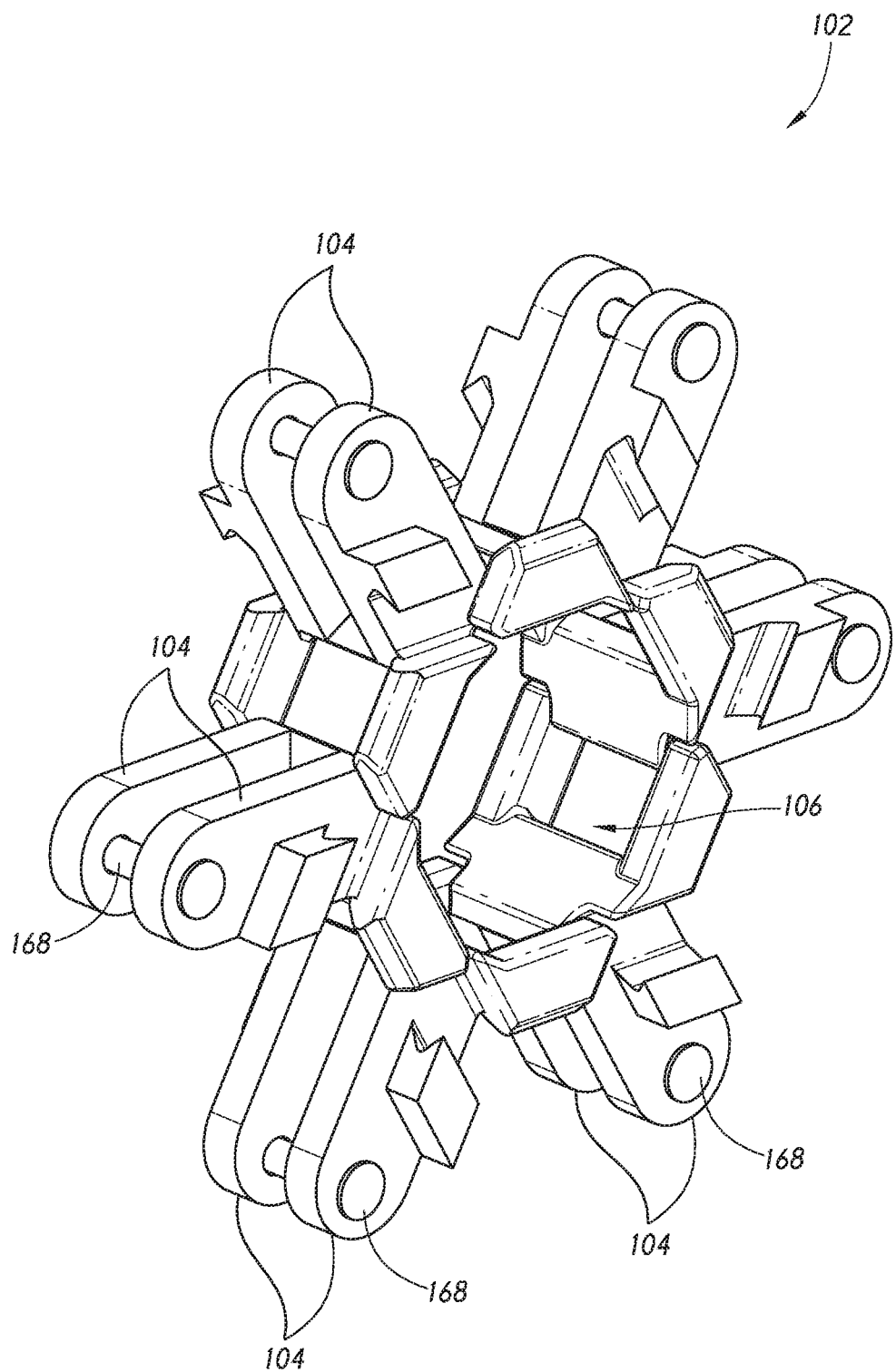
FIG. 5 is a perspective view of a compression assembly of the crimper device of FIG. 1, according to some embodiments.
Figure 6:
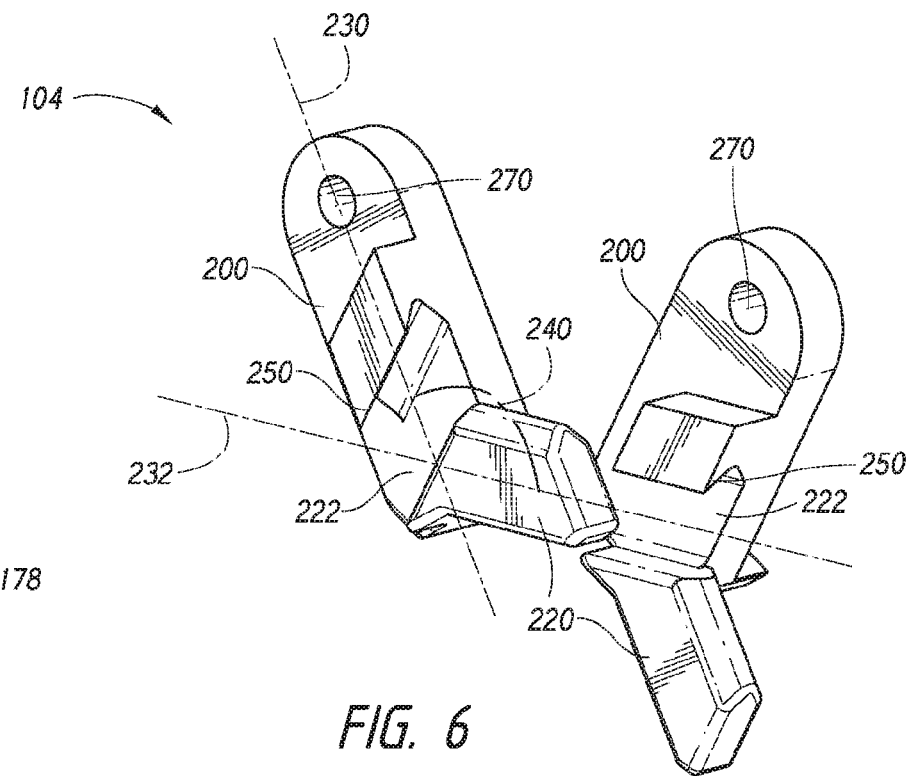
FIGS. 6 and 7 are perspective exterior- and interior-facing views of compression members of the compression assembly of FIG. 5, according to some embodiments.
Figure 7:
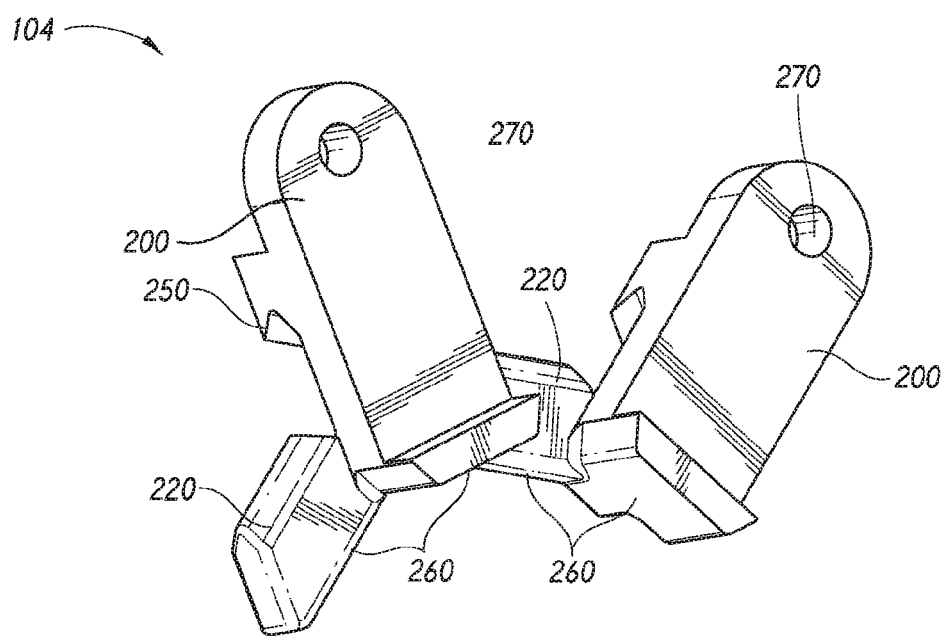

Referring now to FIGS. 5-7, an embodiment of the compression assembly 102 and its individual compression members 104 is shown. The operation and motion of the compression members 104 of the compression assembly 102 has been discussed above. As shown in FIG. 5, the compression members 104 can be positioned adjacent to one another as illustrated to form the compression aperture 106. In accordance with some embodiments, inward radial motion of plurality of compression members 104, which reduces the size of the compression aperture 106, can provide an approximately equal force around the circumference of the compression aperture 106 to provide uniform compaction of a stent frame positioned within the aperture 106. The size of the compression aperture 106 can be defined geometrically as a diameter of the largest circle inscribed in the aperture 106, as measured in the plane of motion of the compression members 104.

The compression assembly 102 can have any number of compression members 104 which can collectively provide an approximately circular central aperture that has an adjustable diameter. The number of compression members 104 shown in FIGS. 1 and 2 is six, but this number can vary such as to be 5-7, 4-8, 3, 4, 5, 6, 7, 8, 9, or 10. As shown in FIGS. 3-5, the number of driving slots 160 and guide slots 162 can be equal to the number of compression members 104 in the device 100.

Further, although the compression members 104 are shown as being evenly spaced around 360-degree compression aperture 106, the compression members 104 can be staggered or otherwise spaced apart at varying angular positions about the compression aperture 106. For example, in some embodiments, one or more compression members can be positioned opposite a fixed surface toward which the one or more compression members can be actuated in order to reduce the size of an aperture formed between the fixed surface and the one or more compression members.

FIGS. 5-7 illustrate that each compression member 104 can comprise a main body 200 that slides within or along the guide/alignment. The main body 200 of each compression member 104 can be positioned within and slide along a flat guide surface 202 (shown in FIG. 4) of a guide slot 162. However, the device 100 can also be configured to permit only a portion of the main body 200 of a compression member 104 to track along or fit within the guide slot 162. Further, the guide slot 162 can also or alternatively comprise a raised ridge or protrusion along which a corresponding slot of a compression member 104 can slide.

In accordance with some embodiments, compression assembly 102 can optionally comprise an axial engagement mechanism. The engagement mechanism can tend to ensure that the compression members 104 of the compression assembly 102 maintain a predetermined or constant axial position relative to the device 100. By so doing, the engagement mechanism can advantageously tend to ensure that no individual compression member 104 is exerting a shear stress along the outer surface of the stent frame during compaction. Further, the engagement mechanism can also advantageously ensure that the compression assembly 102 exerts a uniform radial force against the stent frame and does not break apart or otherwise experience point stresses within the compression assembly 102 itself. For example, in some embodiments, the engagement mechanism can advantageously tend to ensure that the rotational force exerted by the user, and translated to radial motion via pins and slots of the rotational and stationary components 110, 112, is substantially uniformly exerted on and mutually borne by all of the compression members 104 of the compression assembly 102 throughout the motion of the device 100 to the collapsed configuration.

For example, FIGS. 6 and 7 illustrate an embodiment of the engagement mechanism in opposing side, perspective views of two compression members 104 of the compression assembly 102. As illustrated, the engagement mechanism of the compression assembly 102 can be configured such that each compression member 104 comprises an engagement arm 220 that extends from the main body 200 and an engagement slot 222 into which the engagement arm 220 can be received and slide. The engagement arm 220 of each compression member 104 can be attached to the main body 200 of the compression member 104, e.g., at a distal end of the main body 200, as shown in FIGS. 6 and 7. Each compression member 104 can be manufactured as a single, continuous piece comprising the main body 200 and the engagement arm 220 or may be constructed by permanently adhering the main body 200 and the engagement arm 220 together.

The axial engagement mechanism can be actuated as the compression assembly 102 moves toward or away from a collapsed position. For example, as the compression members 104 move radially toward a central axis of the compression assembly 102 (along longitudinal axis 230), the engagement arm 220 of each compression member 104 will slide (along longitudinal axis 232) further into the engagement slot 222. This sliding engagement between the engagement arms 220 and the engagement slots 222 creates an in-plane engagement between all of the compression members 104 of the compression assembly 102. Additionally, the radial inward force exerted on the compression members 104 can be transferred to and from other compression members 104 during actuation of the compression assembly 102. This transfer of radial inward force can occur as engagement arms 220 contact top and bottom portions of engagement slots 222. This transfer can advantageously tend to promote the creation of uniform compressive forces exerted on and by the individual compression members 104.

FIG. 6 also illustrates an embodiment of compression members 104 wherein the main body 200 and the engagement arm 220 are attached to one another at an angle 240 of about 120°. This angle 240 (as measured between the longitudinal axes 230, 232) may vary depending on the number of compression members in the compression assembly. However, the angle 240 between the main body 200 and the engagement arm 220 of a compression member 104 within a constructed compression assembly 102 does not change upon enlarging or reducing the diameter of the compression aperture 106 formed by the simultaneous movement of the plurality of compression members 104.

Also shown in FIGS. 6-7 is a tab structure 250 which protrudes from the upper surface of the main body 200 of each compression member 104 and which contacts the outer edge of the engagement arm 220 of an adjacent compression member 104. The tab structure 250 can be fixed to the upper edge or surface of the engagement slot 222 of the compression member 104. The tab structure 250 can comprise an edge or protrusion that partially encloses the slot 222 or a wall that completely encloses a side of the slot 222. The tab structure 250 can contact the engagement arm 220 passing within the slot 222 and assist in maintaining the arm 220 within the slot 222.

FIG. 7 also illustrates stent contact surfaces 260 of the compression assembly 102. The contact surfaces 260 can be located at ends of the main body 200 of the compression members 104 and/or along ends of the engagement arms 220. The contact surfaces 260 can be planar and/or comprise arcuate surfaces that can approximate a rounded shape as the surfaces 260 converge toward each other as the compression assembly 102 moves to the collapsed configuration.

Furthermore, FIGS. 6 and 7 also illustrate that the main body 200 of the compression member 104 can comprise a driving aperture 270. The driving aperture 270 can be configured to receive a rivet or faster that can sliding Lee coupled the compression member 104 with a respective driving slot 160. As illustrated in FIG. 5, opposing compression members 104 (which can be placed on either side of the rotating guide section 122) can be coupled together using a rivet or fastener having a head portion that is larger than a diameter of the driving aperture 270.

Referring now to FIGS. 8-11, the device 100 can be actuated by rotating the rotatable component 110 toward the stationary component 112. FIGS. 8 and 9 illustrate the device 100 in an open or expanded configuration 300, and FIGS. 10 and 11 illustrate the device 100 in a closed or collapsed configuration 302. Simultaneous radial movement of plurality of compression members 104 can cause enlargement or reduction of the diameter of the compression aperture 106. The maximum size of the compression aperture 106 can be determined in part by the length of the engagement arm 220 of each of the plurality of compression members 104, the length of the guide slots 162, and the length of the driving slots 160. As shown in FIGS. 8-11, inward simultaneous movement of the main body 200 of each of plurality of compression members 104 results in a reduction in the diameter of the compression aperture 106 whereas outward movement of the main body 200 of each of plurality of compression members 104 results in an increase in the diameter of the compression aperture 106. Thus, as shown, a stent frame 310 can be compressed from an expanded configuration to a collapsed configuration.

Figure 12:
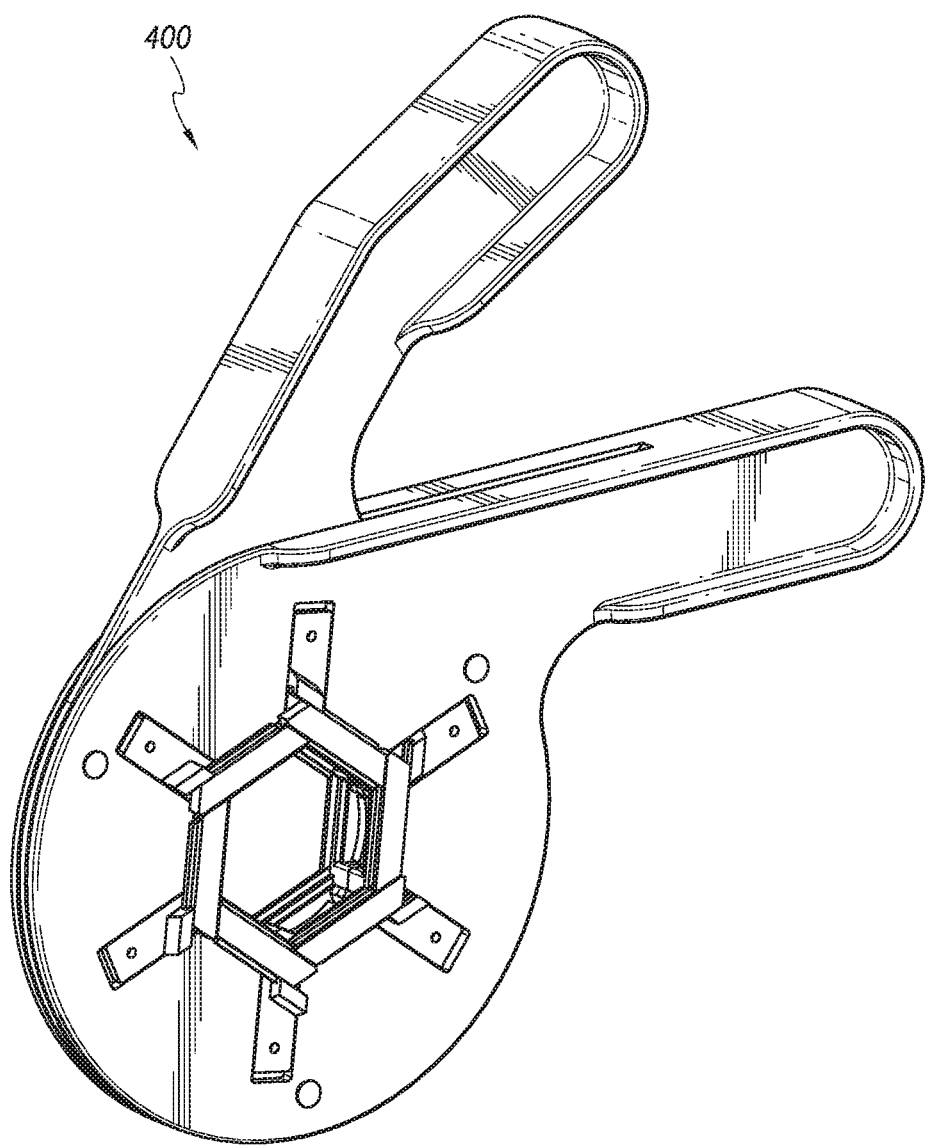
FIGS. 12 and 13 are perspective views of another embodiment of a crimper device in open and closed configurations.
Figure 13:
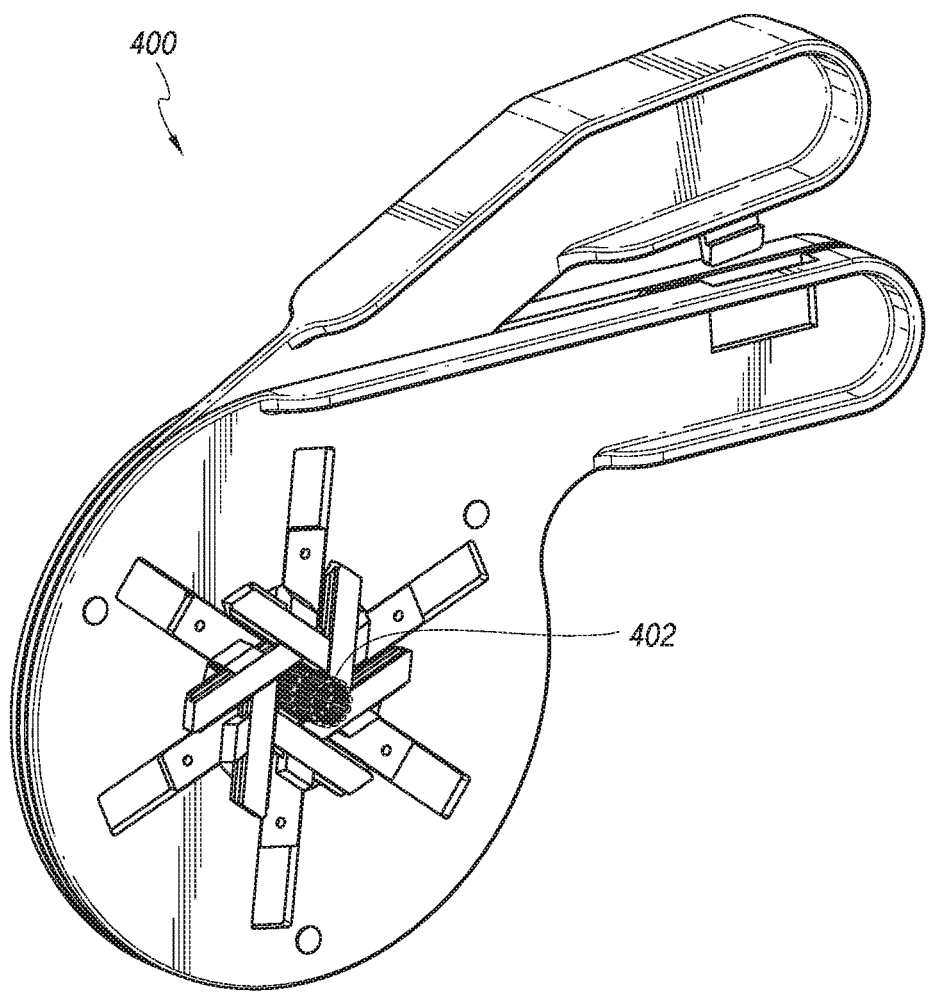

FIGS. 12-15 illustrate another crimper device 400, in accordance with some of the embodiments disclosed herein. The crimper device 400 can have a larger diameter central aperture in order to permit a larger range of diameters of the compression aperture. FIG. 12 illustrates the device 400 and an open configuration, and FIG. 13 illustrates the device 400 in a closed configuration, with a stent frame 402 being collapsed thereby. The device 400 can operate and be configured in a manner similar to the device 100 discussed herein. Accordingly, for brevity of the present disclosure, the details discussed above with respect to the device 100 will not be repeated here and are incorporated by reference herein.

Figure 14:
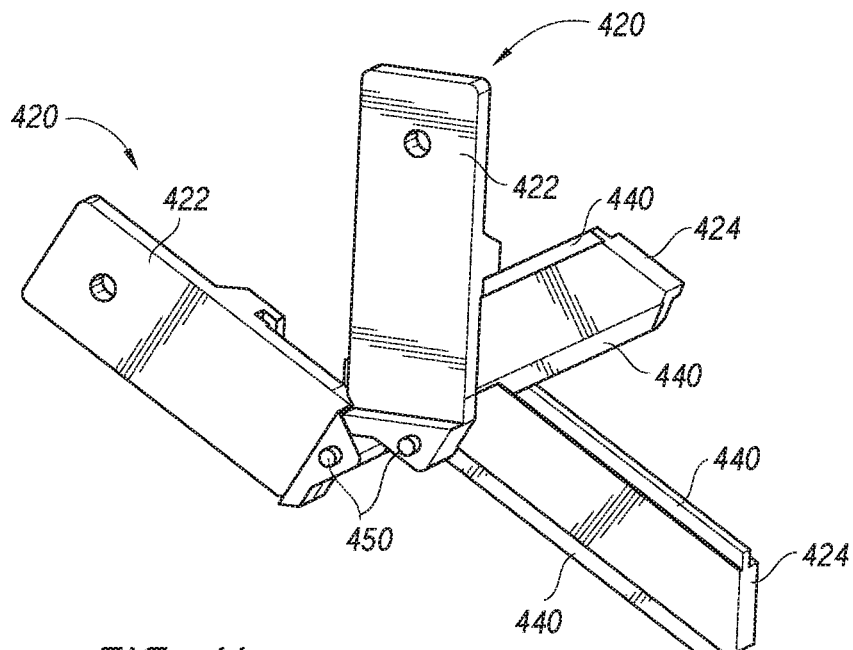
FIGS. 14 and 15 are interior- and exterior-facing views of compression members of a compression assembly of the crimper device of FIG. 12, according to some embodiments.
Figure 15:
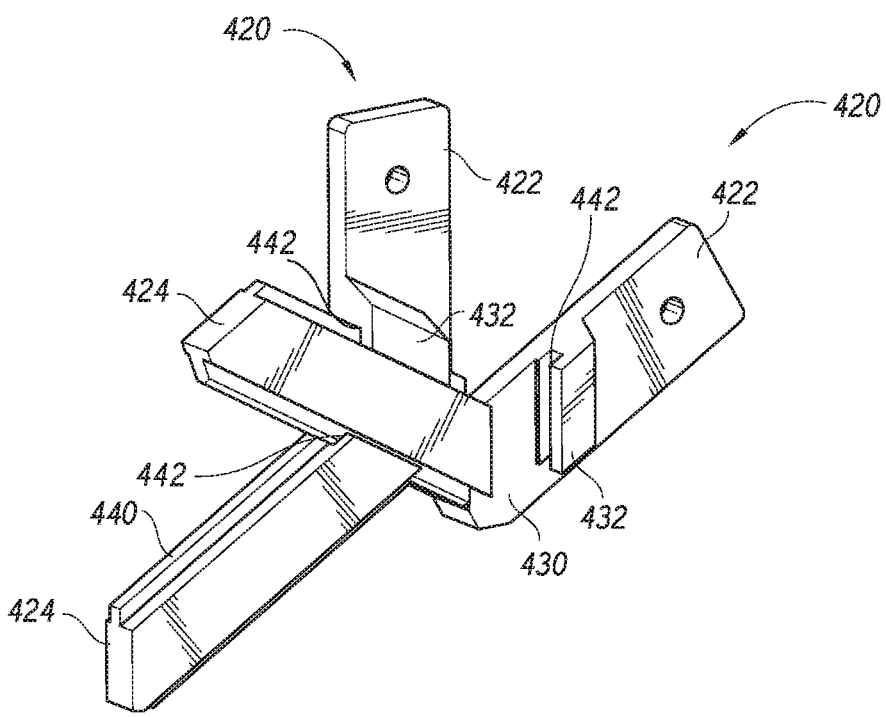

FIGS. 14 and 15 illustrate aspects of compression members 420 of the crimper device 400. Similar to the compression members 104 discussed above, the compression members 420 can comprise a main body 422 and an engagement arm 424 extending from the main body 422. Further, the compression members 420 can also comprise engagement slots 430 that are formed between a tab 432 and a proximal end of the engagement arm 424. Additionally, the engagement arms 424 can optionally comprise a longitudinal ridge 440 that can mate with a corresponding groove 442 in the engagement slot 430. Further, an inside-facing portion of the compression members 420 can be configured to include a coupling pin 450 that can be used to join or individual compression members 420 of a pair of compression members 420 to each other.

Figure 16:
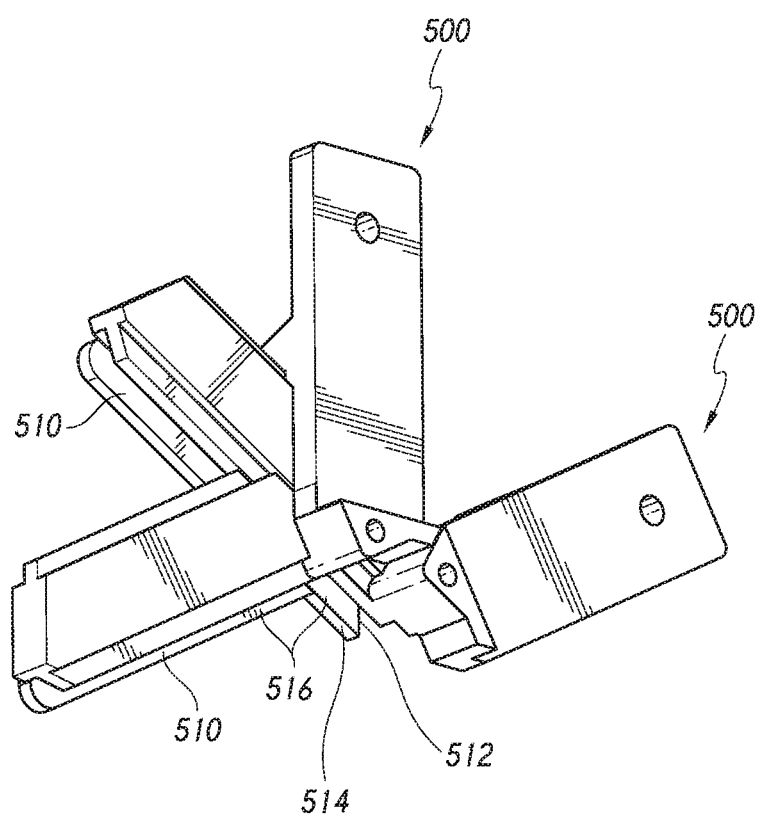
FIG. 16 is a perspective view of other compression members, according to some embodiments.

FIG. 16 illustrates another embodiment of a compression member 500, which includes many of the structural features illustrated with respect to the compression members 420. Additionally, the compression members 500 can further comprise a lip or radial edge portion 510 that extends radially inwardly from the engagement arm and into the compression aperture. The radial edge portion 510 can be used to engage an end of the stent frame and allow the user to exert a longitudinal force on the stent frame. The radial edge portion 510 of adjacent compression members 500 can comprise a proximal end 512 that abuts a bottom surface 514 of a radial edge portion 510 of an adjacent compression member 500. In this manner, the radial edge portions 510 can slide relative to each other and permit the compression members 500 to decrease the size of the compression aperture. Further, because the radial edge portions 510 extend radially inwardly from the compression members 500 (and thus beyond or into the profile of the compression aperture), the radial edge portions 510 can securely contact an end of the stent frame upon which the compression members 500 are acting.

Figure 17:
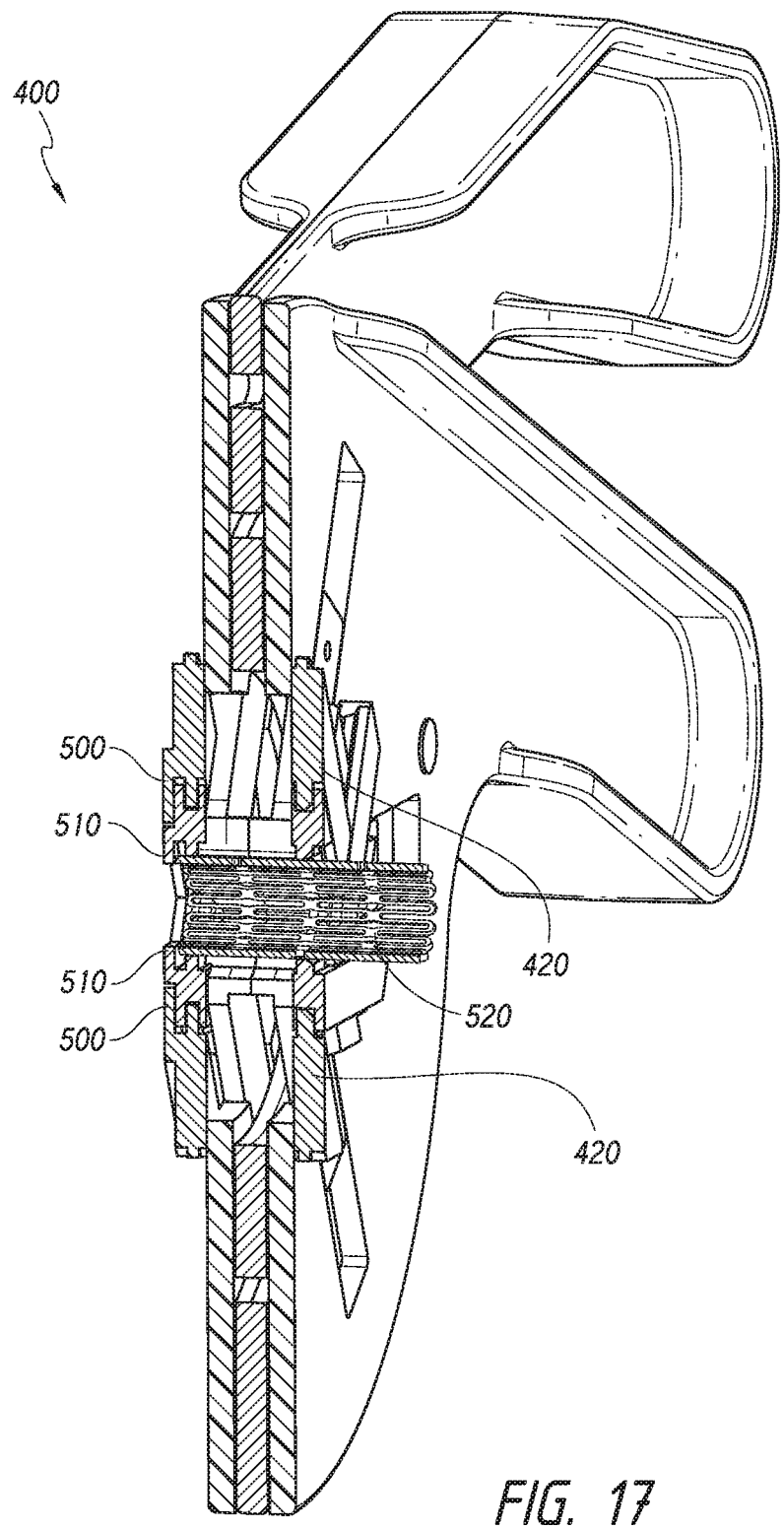
FIG. 17 is a cross-sectional end view of the crimper device of FIG. 12 engaging a stent frame, according to some embodiments.

For example, FIG. 17 illustrates the crimper device 400 having the compression members 420 and 500 engaged with a stent frame 520. As discussed above, during the compression process, the stent frame 520 can be received into the compression aperture and an end or edge of the stent frame can be abutted against a face portion 516 of the radial edge portions 510 of the compression members 500. As the stent frame 520 is collapsed within the compression aperture, the stent frame 520 can tend to longitudinally lengthen in the direction opposite the radial edge portions 510. Further, with the radial edge portions 510 of the compression members 500 in longitudinal abutting contact with a face portion 516 of the end or edge of the stent frame, a longitudinal force can be exerted by the user to push the free, exposed end of the stent frame 520 into engagement with a component of a stent delivery assembly in order to secure the stent frame 520 in a position prepared for delivery.

Optionally, in accordance with some embodiments, the stent frame 520 can be positioned to extend entirely through the aperture, past the radial edge portions 510 of the compression members 500. Thus, instead of longitudinally abutting the face portions 516 of the radial edge portions 510, the bottom surfaces 514 of the radial edge portions 510 can be used to radially contact and compress a select portion of the stent frame 520. This may be useful in order to provide targeted compression around a specific longitudinal section of the stent frame 520 or to otherwise manipulate a profile or shape of the stent frame 520. Thereafter, the crimper can be slightly released, and if needed, the radial edge portions 510 can further be used as discussed above to provide a longitudinal pushing force against an end or edge of the stent frame 520.

As used in this specification, the singular forms "a," "an," and "the" include plural referents unless the context clearly dictates otherwise. Thus, for example, reference to a "compression member" includes a single compression member as well as two or more of the same or different compression members, reference to a "slot" includes a single slot as well as two or more of the same or different slots, and the like.

Where a range of values is provided, it is intended that each intervening value between the upper and lower limit of that range and any other stated or intervening value in that stated range is encompassed within the disclosure. For example, if a range of 115 degrees to 125 degrees is stated, it is intended that 116 degrees, 117 degrees, 118 degrees, 119 degrees, 120 degrees, 121 degrees, 122 degrees, 123 degrees and 114 degrees are also explicitly disclosed.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A device for collapsing a stent frame, the device comprising:
    a stationary first component comprising a first grip section and a first guide section coupled to the first grip section, the first guide section comprising (i) a first central aperture having a first central axis and (ii) a plurality of first elongate guide slots extending in a radial direction from the first central aperture;
    a rotatable second component comprising a second grip section and a second guide section, the second guide section comprising (i) a second central aperture having a second central axis coaxially aligned with the first central axis and (i) a plurality of driving structures extending about the second central aperture;
    an alignment mechanism configured to maintain the second central axis coaxially aligned with the first central axis as the second guide section rotates relative to the first guide section; and
    a plurality of compression members, each comprising a contact surface for engaging an expandable implant, each compression member being slidably positioned at least partially within a respective first elongate guide slot and slidably engaged with a respective driving structure for urging slidable movement of the compression members within the first elongate guide slots as the second guide section rotates relative to the first guide section, thereby moving the contact surfaces between expanded and collapsed positions upon rotation of the second component relative to the first component to increase or decrease a size of a compression aperture formed by the contact surfaces,
    wherein each of the plurality of compression members comprises an axial engagement mechanism having an engagement arm extending radially therefrom and an engagement slot for receiving an adjacent engagement arm of an adjacent compression member, and wherein during movement to a closed configuration, adjacent engagement arms are configured to radially interconnect with adjacent engagement slots to restrict axial movement of the plurality of compression members with respect to each other.

2. The device of claim 1, wherein the alignment mechanism comprises (i) a plurality of alignment slots in the first or second guide sections and (ii) a plurality of alignment rivets coupled to the first or second guide sections and extending through the alignment slots to maintain the second central axis coaxially aligned with the first central axis as the second guide section rotates relative to the first guide section.

3. The device of claim 1, wherein the alignment mechanism comprises a plurality of alignment slots in the second guide section and a plurality of alignment rivets coupled to the first guide section, the plurality of alignment slots extending about the second central aperture, wherein movement of the alignment rivets within the alignment slots maintains the second central axis coaxially aligned with the first central axis as the second guide section rotates relative to the first guide section.

4. The device of claim 1, wherein the plurality of driving structures comprises a plurality of driving slots in the second guide section.

5. The device of claim 4, wherein the plurality of driving structures further comprises a plurality of driving rivets, each coupled to a respective compression member and engaged with the plurality of driving slots for urging slidable movement of the compression members within the first elongate guide slots.

6. The device of claim 1, further comprising a stationary third component comprising a third grip section and a third guide section coupled to the third grip section, the third guide section comprising (i) a third central aperture having a third central axis and (ii) a plurality of third elongate guide slots extending in a radial direction from the third central aperture, the third grip section being coupled to the first grip section to thereby align the third central axis with the first and second central axes and the plurality of third elongate guide slots with the plurality of first elongate guide slots.

7. The device of claim 6, wherein the alignment mechanism comprises (i) a plurality of alignment rivets coupled to both the first and third guide sections and (ii) a plurality of alignment slots in the second guide section, and wherein the second guide section is interposed between the first and third guide sections to thereby align the third central axis with the first and second central axes.

8. The device of claim 1, wherein each of the plurality of compression members comprises a sliding portion in slidable contact with a portion of the respective first guide slot.

9. The device of claim 8, wherein each of the first elongate guide slots comprises a straight edge for contacting respective sliding portions and facilitating straight radial movement of the compression members relative to the second central axis.

10. The device of claim 1, wherein each of plurality of compression members comprises first and second halves, and wherein the rotatable second component is interposed between the first and second halves of each of the compression members.

11. The device of claim 10, wherein the first and second halves of the plurality of compression members are identical.

12. A device for collapsing a stent frame, the device comprising:
    first and second components each having an elongate handle portion and a ring portion, the ring portions each comprising apertures having central axes that are coaxial when the first and second components are coupled together, the first and second components comprising a pin and slot alignment mechanism to permit relative rotation between the first and second components while maintaining the central axes thereof coaxial with each other, wherein the first component comprises guide portions that extend radially outwardly from the central axis of the first component, and wherein the second component comprises driving portions that extend along a circumferential path that converges toward the aperture of the second component; and a plurality of compression members each having a sliding portion and a driven portion, each sliding portion being engaged with a respective guide portion to move radially relative to the central axis of the first component, each driven portion being engaged with a respective driving portion to cause radial movement of the compression member along the guide portion when the first component is rotated relative to the second component, wherein each of the plurality of compression members comprises an engagement slot and an engagement arm extending toward an adjacent engagement slot of an adjacent compression member, and wherein during movement to a closed configuration, adjacent engagement arms are configured to radially interconnect with adjacent engagement slots to restrict axial movement of the plurality of compression members with respect to each other.

13. The device of claim 12, wherein the guide portions of the first component comprise elongate slots, and wherein the sliding portion of each of the plurality of compression members permits each compression member to move radially within a respective elongate slot of the first component.

14. The device of claim 12, wherein the driving portions of the second component comprise driving slots, and wherein the driven portion of each of the plurality of compression members comprises a pin slidable within a respective driving slot of the second component to permit each compression member to move radially within a respective guide slot of the first component.

15. The device of claim 12, wherein the ring portion of the first component comprises opposing halves and an axial space therebetween into which the ring portion of the second component is positioned to coaxially align the central axes of the ring portions of the first and second components.

* * * * *